United States Patent [19]
Reznik et al.

[11] 4,393,872
[45] Jul. 19, 1983

[54] ASPIRATING SURGICAL FORCEPS

[75] Inventors: Benjamin Reznik; Stanley Welber; Ludwig Streifeneder, all of Chicago, Ill.

[73] Assignee: Eder Instrument Co., Inc., Chicago, Ill.

[21] Appl. No.: 153,181

[22] Filed: May 27, 1980

[51] Int. Cl.³ .............................................. A61M 1/00
[52] U.S. Cl. .............................. 604/151; 128/303 R; 128/321; 128/752
[58] Field of Search .......... 128/4, 303 A, 321, 303 R, 128/276, 752, 753, 754, 240

[56] References Cited
U.S. PATENT DOCUMENTS

| | | | |
|---|---|---|---|
| 836,217 | 11/1906 | Rowe | 128/324 |
| 2,114,695 | 4/1938 | Anderson | 128/321 |
| 2,137,710 | 11/1938 | Anderson | 128/321 |
| 2,670,519 | 3/1954 | Recklitis | 27/24 |
| 3,820,544 | 6/1974 | Semm | 128/326 |
| 3,835,842 | 9/1974 | Iglesias | 128/7 |
| 3,934,589 | 1/1976 | Zimmer | 128/321 |
| 4,103,680 | 8/1978 | Yoon | 128/303.15 |
| 4,174,715 | 11/1979 | Hasson | 128/321 |
| 4,257,419 | 3/1981 | Goltner | 128/326 |
| 4,261,346 | 4/1981 | Wetterman | 128/6 |

Primary Examiner—Richard J. Apley
Assistant Examiner—J. L. Kruter
Attorney, Agent, or Firm—McDougall, Hersh & Scott

[57] ABSTRACT

A surgical forceps is provided having the ability, in addition to the normal grasping function, to simultaneously aspirate a liquid from a surgical site. An inner tubular member has a plurality of prongs and is slidably disposed within a tubular body. The inner tubular member is spring loaded so as to hold the prongs in a normally retracted position substantially within the body. A center channel extends throughout the instrument enabling liquids to be aspirated. The prongs diverge as they are extended by forward movement of the inner tubular member and converge upon retraction.

11 Claims, 5 Drawing Figures

FIG. 4

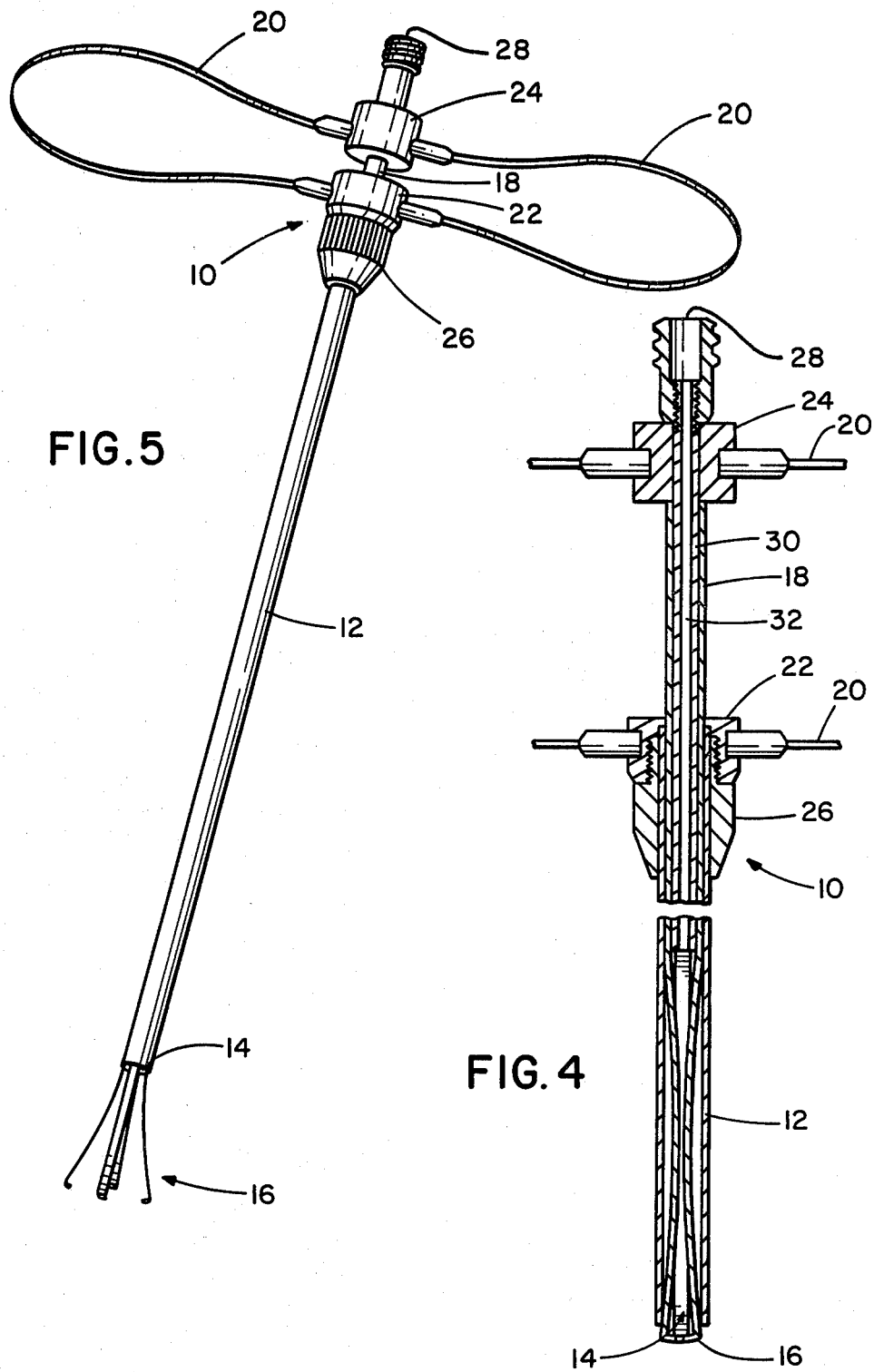

ASPIRATING SURGICAL FORCEPS

BACKGROUND OF THE INVENTION

This invention relates generally to the field of surgical instruments, and more specifically, to grasping forceps.

Arthroscopy is a relatively new medical procedure allowing a physician to examine the interior of a joint by means of a small incision through which an arthroscope (endoscope) is inserted. The arthroscope is an optical instrument which enables a physician to visually inspect the interior of a joint without making a conventional surgical opening. When unattached bone fragments are discovered within a joint, as in the case of a chip fracture, an arthroscopic procedure allows removal of such fragments. This is achieved by forming a second small incision, permitting insertion of an additional surgical instrument into the joint. The primary objective of the additional instrument is the removal of bone fragments utilizing grasping forceps of a conventional design.

The present invention provides such an additional instrument with grasping forceps offering several advantages. These advantages will be apparent from the remainder of this specification.

PRIOR ART STATEMENT

The following prior art constitutes the closest known art to the instant invention.

U.S. Pat. No. 2,670,519 to C. F. Recklitis discloses an embalming instrument used to extract blood. This instrument utilizes three extendable fingers to remove blood clots that may form at the mouth of the instrument.

U.S. Pat. No. 4,174,715 to Harrith M. Hasson discloses a spring-loaded laparoscopy instrument having a plurality of prongs. One embodiment of such an instrument is provided with a central bore for facilitating ovarian biopsy.

The following United States Patents are cited as disclosing conventional grasping forceps: U.S. Pat. No. 836,217 to Rowe; Nos. 2,114,695 and 2,137,710 to Anderson.

SUMMARY OF THE INVENTION

A surgical instrument is provided which allows continuous aspiration of a surgical site while simultaneously grasping tissue or objects. A tubular body houses an actuating tube slidably disposed therein. A plurality of springy prongs are integrally formed from one end of the tube and may be substantially retracted within the tubular body. The prongs upon being extended outwardly from the mouth of the body diverge; upon retraction, the prongs converge enabling objects to be captivated. Sliding the tube back and forth within the body controls the extension and retraction of the prongs. A hollow interior within the tube provides a passage for the aspiration of liquids. The configuration of the prongs permits the flow of fluids even while retracted. The tube is spring loaded to hold the prongs in a normally retracted position. The rearward end of the instrument has an outlet port which permits connection to an evacuation pump through a flexible tube. Thus, fluids are sucked through this instrument from a surgical site. The embodiment of the present invention is especially adapted to capturing and removing bone chips from a joint using arthroscopic surgical techniques.

It is a primary object of the present invention to provide surgical forceps capable of simultaneous aspiration and having spring-loaded extendable prongs which may be quickly retracted so as to capture a bone chip or foreign particle floating within the liquid being aspirated.

BRIEF DESCRIPTION OF THE DRAWINGS

FIG. 4 is a fragmentary cross-sectional side view taken along line 4—4 in FIG. 1.

FIG. 5 is an isometric view illustrating the embodiment of the present invention with the prongs in an extended position.

DETAILED DESCRIPTION

Figure 1:
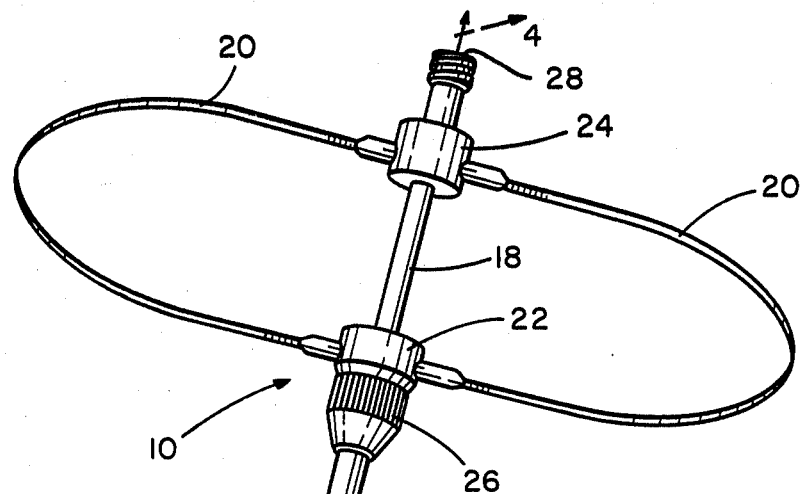
FIG. 1 is an isometric view of an instrument embodying the present invention illustrating the prongs in a retracted position.

As shown in FIG. 1, the embodiment of the present invention, designated generally as numeral 10, has a tubular body 12, having one end which defines a mouth 14. A plurality of prongs 16 are shown in a retracted position extending only slightly beyond mouth 14. The prongs are integrally formed from one end of inner tube 18 which is slidably disposed within tubular body 12. A pair of springs 20 have each of their ends mounted to spring carriers 22 and 24 respectively. Carrier 22 is held stationary with respect to body 12 by engagement with collar 26 and has an opening permitting tube 18 to freely pass therethrough. Carrier 24 is immovably connected to tube 18. A port 28 provides a means for coupling a suction tube thereto for evacuating liquids entering mouth 14 through a hollow path inside tubular body 12 and inner 18.

FIG. 5 is similar to the illustration of the preferred embodiment shown in FIG. 1 except that instrument 10 is shown in an extended position with prongs 16 extending outwardly from mouth 14. This extension is accomplished by sliding inner tube 18 forward toward mouth 14. It will be noticed that spring carrier 22 which is fixed relative to body 12 and carrier 24 which is fixed relative to tube 18 are closer together in FIG. 5 than as shown in FIG. 1. This indicates that tube 18 has been slid forward within body 12. Springs 20 are compressed and present forces opposing the forward movement of tube 18. In practice, a physician will manually operate this instrument, i.e. cause the extension of the prongs. A sudden release of the force applied by the physician to overcome the spring forces will cause prongs 16 to be quickly retracted.

Figure 2:
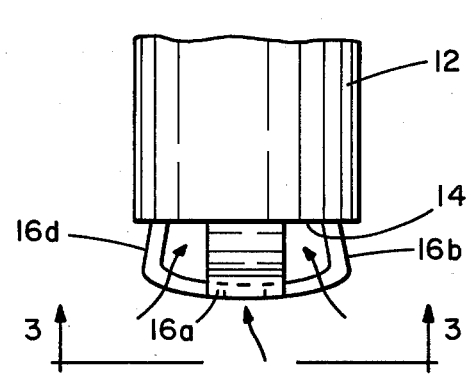
FIG. 2 is a fragmentary side view of the end of this instrument illustrating the prongs in a retracted position.
Figure 3:
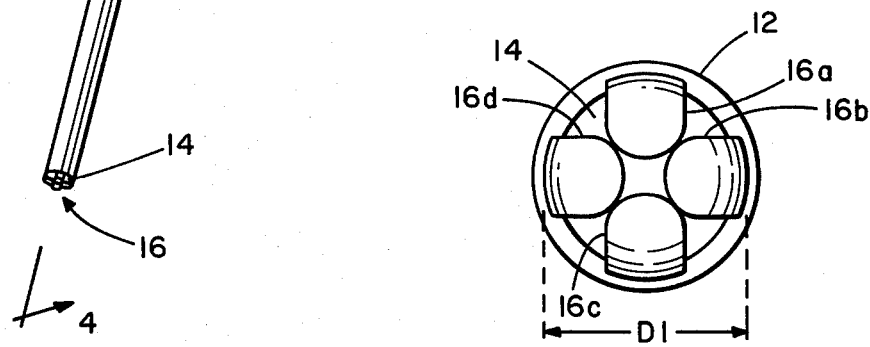
FIG. 3 is an end view along line 3—3 in FIG. 2.

FIGS. 2, 3 and 5 best illustrate the configuration of prongs 16. Now referring in particular to FIGS. 2 and 3, prongs 16 are shown in the normally retracted position. Four prongs 16a, 16b, 16c and 16d are shown extending slightly beyond mouth 14 of tubular body 12 and having inwardly bent distal ends which are blunt. Each of prongs 16a through 16d are of equal length and have ends which abut the ends of adjoining prongs in the retracted position. The arrows as shown in FIG. 2 illustrates that even while retracted the prongs leave substantial openings for the flow of fluids into mouth 14.

The inwardly turned ends of prongs 16a–16d serve at least two purposes. First, they enable the physician to more readily grasp or grip tissue and capture objects therebetween. Secondly, the inwardly turned ends of the prongs act as a stop to prevent springs 20 from pulling the prongs completely within tubular body 12. The length of the inwardly turned ends of the prongs is such that when adjacent ends of the prongs abut as shown in FIG. 3, the total expanse indicated as distance D1 in FIG. 3 exceeds the inside diameter of tubular body 12 thereby peventing the prongs from being completely withrawn therein. Thus, the prongs wedge against the inside of tubular body 12 at mouth 14 to restrict the rearward movement of inner tube 18 as urged by springs 20.

Now referring to FIG. 4, the detailed construction of instrument 10 is shown. Prongs 16 are integrally formed from one end of inner tube 18 and are bent arcuately outward so as to diverge upon being extended beyond mouth 14. The prongs are thus bowed inwardly in the retracted position. The outside diameter of inner tube 18 is slightly less than the inside diameter of tubular body 12 thereby enabling the inner tube to freely slide within the body. Collar 26 is permanently attached near the rearward end of body 12. Spring carrier 22 has a hole permitting tube 18 to freely pass therethrough and has a larger diameter bore internally threaded so as to mate with external threads on collar 26. Thus, carrier 22 is threadedly connected with collar 26 thereby operatively connecting the lower ends of springs 20 to body 12.

A center tube 30 is fixedly mounted within inner tube 18. Center tube 30 extends foward to the point of beginning of prongs 16 and rearward beyond the extent of tube 18 with the rearward extent of center tube 30 being externally threaded. Spring carrier 24 has a cylindrical opening allowing center tube 30 to pass therethrough but abutting inner tube 18. Port 28 has a cylindrical opening therethrough and threadedly engages center tube 30 so as to lock spring carrier 28 in fixed relationship with inner tube 18. The rearward outside periphery of port 28 is grooved in a conventional manner so as to facilitate an air-tight connection with an evacuation tube to be inserted thereover.

In practice, the evacuation tube would be connected to a vacuum pump enabling liquids to be sucked into mouth 14 and through interior channel 32 of instrument 10. Channel 32 comprises the central opening extending from mouth 14 through the hollow interior of center tube 30 and outwardly through port 28. Preferably, all materials used in constructing instrument 10 can withstand being autoclaved to achieve sterilization. In addition, spring 20 and inner tube 18, from which prongs 16 are integrally made, should be resilient and springy. The preferred material for constructing instrument 10 is stainless steel which is able to withstand autoclaving and is sufficiently springy to form prongs 16 and springs 20.

OPERATION

Because the preferred embodiment of the present invention has particularly useful application in arthroscopic surgery, an example of its utilization in this regard follows. For purposes of example, assume that a knee joint has sustained a traumatic fracture causing chip fractures (unattached bone fragments) to be present within the joint. A small incision is made permitting an arthroscope to be inserted into the joint area for visual inspection. An arthroscope normally has at least one channel which may be utilized to irrigate the joint with a liquid.

Port 28 of instrument 10 is connected to a resilient evacuation hose (not shown) which is, in turn, connected to a source of vacuum such as a pump which creates a vacuum through the center channel 32 of the instrument tending to suck fluids into mouth 14 and out through the instrument. A second small incision is made at the knee joint permitting the mouth of body 12 to be inserted into the joint with the prongs in the retracted position. A channel located within the arthroscope is then utilized to irrigate the joint and a suction is applied to the hose connecting instrument 10 to aspirate the applied liquid. By utilizing the arthroscope to see inside the irrigated joint, the surgeon visually locates the bone chips dispersed in the liquid. Because the liquid is being sucked into mouth 14 of instrument 10, there is a natural tendency to pull the bone chips floating in the liquid towards mouth 14. With the prongs in an extended position and while viewing the joint through the arthroscope, any large bone chips may be readily captured by allowing the prongs to quickly retract thereby captivating the chips therebetween. Instrument 10 is then removed from the joint and the bone fragment dislodged by extending the prongs. The instrument may be reinserted to capture further chip fragments. Relatively small bone fragments or chips may be sucked directly through the instrument without requiring its removal from the joint.

While any type of surgical instrument capable of grasping relatively small objects could be utilized to grasp the floating bone chips, it is often difficult from a practical standpoint to physically grasp the chips due to the turbulence of the liquid. Because aspiration is concurrently employed with the instant evacuating forceps, the floating bone fragments tend to drift towards the mouth of the instrument where they may be readily trapped by the prongs.

From the above, it will be apparent that the present invention offers several advantages. The instrument embodying the present invention may be autoclaved as a standard surgical instrument to achieve sterilization. The straightforward design and the relatively few separate parts used to construct the present instrument enhances reliability as well as achieves ease of manufacture and assembly. The degree of difficulty in grasping unattached particles while floating in a liquid is significantly reduced since the particles will naturally tend to be drawn towards the mouth of the instrument during aspiration, simplifying captivating the particles by the prongs. Although the instrument of this invention is particularly useful in the field of arthroscopy, its range of utilization is not limited thereto.

Although an embodiment of the present invention has been shown and described in such detail as to allow one skilled in the art to practice this invention, it is to be understood that various modifications and substitutions may be mde by those skilled in the art without departing from the scope of the invention as defined by the claims appended hereto.

What is claimed is:

1. Surgical forceps capable of simultaneously aspirating liquids from a surgical site while grasping objects such as bone chips floating in said liquid, said forceps comprising:

(a) an elongate tubular body defining a channel which terminates at one end of said body to define a mouth;
(b) at least three springy prongs having inwardly bent distal ends;
(c) an actuating means disposed within the body for retracting said prongs substantially within the mouth of the channel and for extending said prongs outwardly from said mouth, said prongs diverging during outward extension and converging during retraction;
(d) a spring means cooperating with said actuating means for normally maintaining the prongs in a retracted position; and
(e) communication means within said body for allowing liquids to be aspirated from a surgical site through said mouth and channel while said prongs are extended, while said prongs are in said retracted position and while said prongs are intermediate said extended and retracted positions, whereby liquids are aspirated such that objects floating in the liquid are drawn towards the mouth facilitating the capture of such objects with said prongs.

2. The forceps according to claim 1 wherein the inwardly bent ends of the prongs converge during retraction to abut adjacent prong ends before said ends reach said mouth.

3. The forceps according to claim 2 wherein the expanse across the abutted ends of the prongs is greater than the expanse of said mouth, whereby the ends of the prongs act as a stop to prevent the ends of the prongs from being retracted by said spring means within the mouth.

4. The forceps according to claim 2 wherein said bent ends of the prongs have a configuration which enables said liquid to be aspirated even during abutment of the adjacent ends.

5. The forceps according to claim 2 wherein four equally spaced prongs converge during retraction to abut adjacent prong ends before said ends reach said mouth.

6. The forceps according to claim 1 wherein said actuating means comprises a tube slidably disposed within said elongate body.

7. The forceps according to claim 6 wherein said prongs are integrally formed from said tube.

8. The forceps according to claim 1 wherein said spring means comprises at least one resilient metal strap having one end fixedly mounted with respect to the tubular body and the other end fixedly mounted with respect to the actuating means.

9. The forceps according to claim 8 further comprising a second metal strap mounted generally opposite said one metal strap to said tubular body and actuating means, said one strap and said second strap defining a handle for holding said forceps.

10. The forceps according to claim 1 wherein said communication means comprises a straight central channel which extends the length of said body, and an outlet port at the other end of said body connected to said central channel for removing the aspirated liquids therefrom.

11. The forceps according to claim 1 wherein the tubular body, prongs, actuating means, spring means, and communication means are made of a material which can withstand autoclaving.

* * * * *